(12) United States Patent
Khalfallah et al.

(10) Patent No.: US 9,636,036 B2
(45) Date of Patent: May 2, 2017

(54) ELECTROPHYSIOLOGICAL ANALYSIS SYSTEM

(71) Applicant: IMPETO MEDICAL, Paris (FR)

(72) Inventors: Kamel Khalfallah, Paris (FR); Philippe Brunswick, Paris (FR)

(73) Assignee: IMPETO MEDICAL, Paris (FR)

( * ) Notice: Subject to any disclaimer, the term of this patent is extended or adjusted under 35 U.S.C. 154(b) by 6 days.

(21) Appl. No.: 14/424,704

(22) PCT Filed: Aug. 27, 2013

(86) PCT No.: PCT/EP2013/067678
§ 371 (c)(1),
(2) Date: Feb. 27, 2015

(87) PCT Pub. No.: WO2014/033105
PCT Pub. Date: Mar. 6, 2014

(65) Prior Publication Data
US 2015/0216441 A1      Aug. 6, 2015

(30) Foreign Application Priority Data
Aug. 28, 2012   (FR) .................................... 12 58037

(51) Int. Cl.
*A61B 5/053*       (2006.01)
*A61B 5/00*        (2006.01)

(52) U.S. Cl.
CPC .......... *A61B 5/0531* (2013.01); *A61B 5/6801* (2013.01); *A61B 5/7225* (2013.01)

(58) Field of Classification Search
CPC ............................ A61B 5/0531; A61B 5/7225
See application file for complete search history.

(56) References Cited

U.S. PATENT DOCUMENTS 3,449,080 A    6/1969   Edwards
3,821,949 A    7/1974   Hartzell et al.
(Continued)

FOREIGN PATENT DOCUMENTS

FR          2912893 A1       8/2008
WO      WO-00/19894 A1       4/2000
WO   WO-2004/043247 A1       5/2004

OTHER PUBLICATIONS

Allen, John: "Topical Review; Photoplethysmography and its application in clinical physiological measurement," IOP Publishing, vol. 28, No. 3. Mar. 1, 2007, pp. R1-R39.
(Continued)

*Primary Examiner* — Michael C Stout
(74) *Attorney, Agent, or Firm* — Harness, Dickey & Pierce, P.L.C.

(57) ABSTRACT

The disclosure relates to an electrophysiological analysis system including: a series of electrodes intended to be placed in different regions of the human body; a direct current voltage source; a control device adapted (i) to selectively apply direct current pulses, generated by the voltage source, to a pair of so-called active electrodes, the active electrodes forming an anode and a cathode, and (ii) to connect at least one other so-called passive electrode with high-impedance, the electrode measuring the potential reached by the body; and a measurement device arranged to obtain data representative of the current at the cathode and the potentials on at least some of the electrodes connected with high impedance, in response to the application of the pulses, which data can be used to determine a value for the electrochemical conductance of the skin. The system also includes a device for controlling the difference between the potential at the anode and the potential reached by the body, (Continued)

according to the voltage delivered by the direct current voltage source.

17 Claims, 6 Drawing Sheets

(56) References Cited

U.S. PATENT DOCUMENTS

| | | | |
|---|---|---|---|
| 4,365,637 A | 12/1982 | Johnson | |
| 4,509,531 A | 4/1985 | Ward | |
| 4,690,152 A | 9/1987 | Juncosa | |
| 4,794,934 A | 1/1989 | Motoyama et al. | |
| 5,307,817 A | 5/1994 | Guggenbuhl et al. | |
| 5,406,956 A | 4/1995 | Farwell | |
| 5,771,261 A | 6/1998 | Anbar | |
| 5,782,884 A | 7/1998 | Stotts et al. | |
| 5,800,350 A | 9/1998 | Coppleson et al. | |
| 5,928,155 A | 7/1999 | Eggers et al. | |
| 6,175,752 B1 | 1/2001 | Say et al. | |
| 6,299,583 B1 | 10/2001 | Eggers et al. | |
| 6,336,045 B1 | 1/2002 | Brooks | |
| 6,473,641 B1 | 10/2002 | Kodama et al. | |
| 6,491,647 B1 | 12/2002 | Bridger et al. | |
| 6,512,949 B1 | 1/2003 | Combs et al. | |
| 6,577,893 B1 | 6/2003 | Besson et al. | |
| 6,871,084 B1 | 3/2005 | Kingsley et al. | |
| 7,161,362 B2 | 1/2007 | Shambroom et al. | |
| 7,477,937 B2 | 1/2009 | Iijima et al. | |
| 7,931,592 B2 | 4/2011 | Currie et al. | |
| 8,085,144 B2 | 12/2011 | Appelt et al. | |
| 8,655,443 B2 | 2/2014 | Brunswick et al. | |
| 8,918,170 B2 | 12/2014 | Brunswick et al. | |
| 8,934,954 B2 | 1/2015 | Brunswick et al. | |
| 8,965,497 B2 | 2/2015 | Tournefier et al. | |
| 2002/0107452 A1 | 8/2002 | Kwong | |
| 2004/0128088 A1 | 7/2004 | Laletin et al. | |
| 2004/0158167 A1* | 8/2004 | Smith | A61B 5/053 600/547 |
| 2005/0113650 A1 | 5/2005 | Pacione et al. | |
| 2005/0245839 A1 | 11/2005 | Stivoric et al. | |
| 2006/0085049 A1 | 4/2006 | Cory et al. | |
| 2006/0127964 A1 | 6/2006 | Ford et al. | |
| 2007/0124176 A1 | 5/2007 | Jung et al. | |
| 2007/0178167 A1 | 8/2007 | Andrijauskas | |
| 2009/0054742 A1 | 2/2009 | Kaminska et al. | |
| 2009/0318779 A1 | 12/2009 | Tran | |
| 2010/0081941 A1 | 4/2010 | Naghavi et al. | |
| 2010/0274113 A1* | 10/2010 | Brunswick | A61B 5/05 600/372 |
| 2013/0053673 A1 | 2/2013 | Brunswick | |
| 2013/0204103 A1 | 8/2013 | Maarek | |

OTHER PUBLICATIONS

Atkins, Peter, et al.; "Atkins' Physical Chemistry," Eighth Edition, 2006, pp. 1-1053.
Awad, Aymen A. et al.; "The Relationship Between the Photoplethysmographic Waveform and Systemic Vascular Resistance," Journal of Clinical Monitoring and Computing, vol. 21, No. 6, Oct. 17, 2007, pp. 365-372.
Brunswick, P., et al.; "Use of Ni electrodes chronoamperometry for improved diagnostics of diabetes and cardiac disease;" Proceedings of the 29th Annual International Conference of the IEEE EMBS, Lyon France, Aug. 23-26, 2007; pp. 4544-4547.
Chizmadzhev, Yuri A., et al.; "Electrical Properties of Skin at Moderate Voltages: Contribution of Appendageal Macropores," Biophysical Journal, vol. 74, Feb. 1998, pp. 843-856.
Cronin, Jane; Mathematics of Cell Electrophysiology, vol. 63, 1981, p. 23.
Gin, H., et al.; "Non-invasive and Quantitative Assessment of Sudomotor Function for Peripheral Diabetic Neuropathy Evaluation," Diabetes Metab, 2011, doi: 10.1016/j.diabet.2011.05.003, six pages.
Hubert, Dominique, et al.; "Abnormal electrochemical skin conductance in cystic fibrosis," Journal of Cystic Fibrosis, doi; 10:1016/j.jcf.2010.09.002, 2010, seven pages.
Khalfallah, K. et al.; "Noninvasive Galvanic Skin Sensor for Early Diagnosis of Sudomotor Dysfunction: Application to Diabetes," IEEE Sensors Journal, vol. 12, No. 3, Mar. 2012, pp. 456-463.
Li, Jin et al; "Computation of Cardiac Output by Pulse Wave Contour," IEEE, 2007, pp. 1088-1090.
Mayaudon, H. et al.; "A new simple method for assessing sudomotor function: Relevance in type 2 diabetes," Diabetes & Metabolism 36 (2010), Mar. 31, 2010, pp. 450-454.
Millasseau, Sandrine C. et al.; "Contour analysis of the photoplethysmographic pulse measured at the finger," Journal of Hypertension, vol. 24, No. 8, Aug. 2006, pp. 1449-1456.
Wang, L. et al.; "Noninvasive Cardiac Output Estimation Using a Novel Photoplethysmogram Index," 31st Annual International Conference of the IEEE EMBS, Minneapolis, MN, Sep. 2-6, 2009, pp. 1746-1749.

* cited by examiner

ELECTROPHYSIOLOGICAL ANALYSIS SYSTEM

CROSS-REFERENCE TO RELATED APPLICATIONS

This application is a National Phase Entry of International Application No. PCT/EP2013/067678, filed on Aug. 27, 2013, which claims priority to French Patent Application Ser. No. 1258037, filed on Aug. 28, 2012, both of which are incorporated by reference herein.

BACKGROUND

The invention relates generally to the field of electrophysiological analysis of the human body, with a view for example to detecting medical conditions. The invention is particularly applicable to evaluating sudomotor function in the human body.

The applicant previously proposed in the patent FR 2 912 893 an electrophysiological analysis system comprising a series of electrodes intended to be placed in different regions of a subject's body, a direct current voltage source, suitable for generating adjustable direct current pulses, and a switching circuit, arranged to selectively connect a pair of so-called active electrodes to the voltage source, said active electrodes forming an anode and a cathode, and to connect at least one other electrode with high impedance. The voltage applied by the voltage source to the electrodes is suitable for generating in the outer layer of the skin an electrophysiological current wherein the study of certain characteristics may indicate the existence of medical conditions or predisposition to medical conditions.

Figure 1:
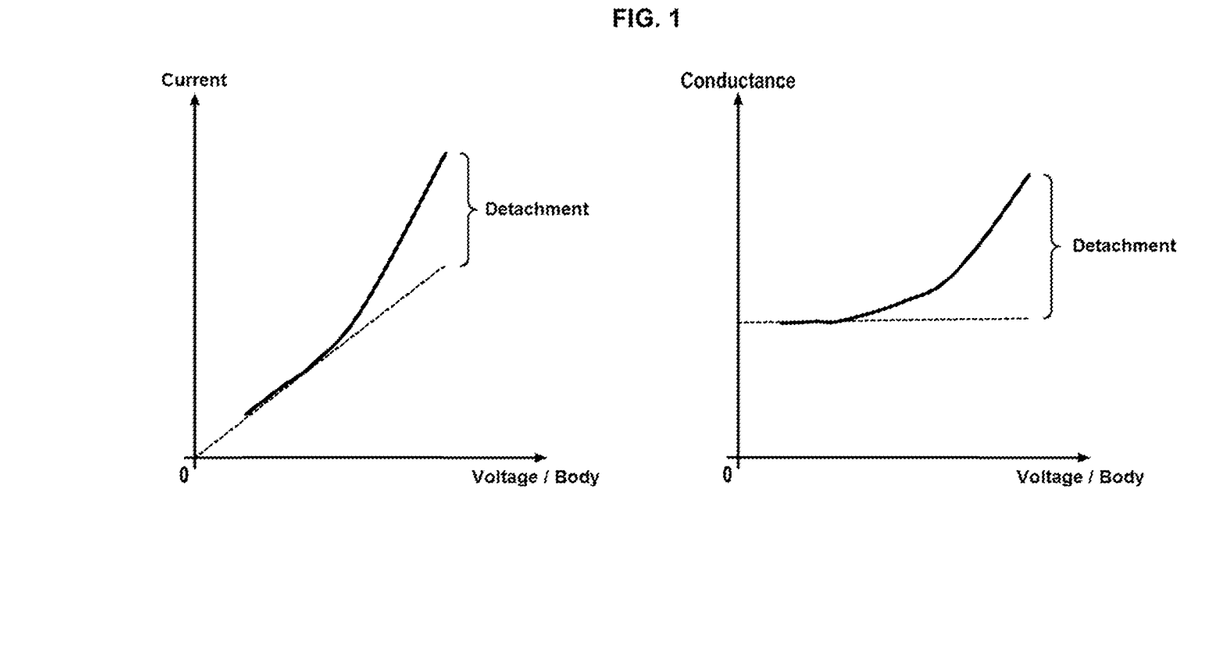
FIG. 1, described above, represents an example of current-conductance-voltage response of human skin.

In particular, and with reference to FIG. 1, the current generated in the skin by applying a voltage is suitable for studying the electrical behaviour of the subject's sweat glands, by measuring the conductance of these glands. This conductance, corresponding to the slope of the voltage-current curve, for the lowest voltages (see patent application FR1160601), varies according to the subject's state of health. In this way, for example, a low voltage-current slope may be an indication, in a diabetic subject, of diabetic neuropathy, as described in the document by Gin H, et al. "Non-invasive and quantitative assessment of sudomotor function for peripheral diabetic neuropathy evaluation. Diabetes Metab (2011), doi:10.1016/j.diabet.2011.05.003".

It has also been observed that the voltage-current curve has, for the lowest voltage levels, a linear portion, followed by a non-linear detachment at higher levels, see FIG. 1. A corresponding detachment takes place for the skin conductance according to the voltage level applied to the body. This detachment does not occur in the same way for different types of subjects, according to any disease from which they suffer, such that the study of this detachment in a subject could be suitable for inferring information on the subject's state of health. However, this detachment does not occur, from one subject to another, on applying the same voltage or for the same current; on the contrary, the inventors observed that the occurrence thereof was dependent on the potential reached by the body and more specifically the difference in potential on either side of the gland, i.e. between the electrode and the body. It is thus suitable to determine this detachment, for all subjects, at the same difference in potential between the electrode and the body.

However, current systems are merely suitable for having access to the difference in potential between the electrode and the potential reached by the body and may not in principle apply this difference in potential, such that the measurements are not made for a constant difference in potential. These systems are thus not suitable for making full use of the voltage-current curve in terms of the detachment thereof to obtain information on the subject's state of health.

SUMMARY

The aim of the present invention is that of remedying the shortcomings described above, by providing a system for studying the detachment of the curve of the sweat glands of various subjects for identical differences in potential. In this respect, the invention relates to an electrophysiological analysis system comprising:
  a series of electrodes intended to be placed in different regions of the human body,
  a direct current voltage source,
  a control device, suitable for selectively applying direct current pulses, generated by the voltage source, to a pair of so-called active electrodes, said active electrodes forming an anode and a cathode, and for connecting at least one other so-called passive electrode with high impedance, said electrode serving to measure the potential reached by the body, and
  a measurement device arranged to obtain data representative of the current at the cathode and the potentials on at least some of the electrodes connected with high impedance, in response to the application of the pulses, said data being suitable for determining a value of the electrochemical conductance of the skin,
  the system being characterised in that it further comprises a device for controlling the difference between the potential of the anode and the potential reached by the body, according to the voltage delivered by the direct current voltage source.

Advantageously, but optionally, the system according to the invention may further comprise at least one of the following features:
  the control device comprises an amplifier circuit between the direct current voltage source and one of the active electrodes, with a feedback loop controlling the gain thereof.
  The anode is connected to the ground, and the amplifier circuit comprises an operational amplifier wherein:
    the inverting input receives the potential reached by the body,
    the non-inverting input is connected to a negative direct current voltage source, and
    the output is connected to the cathode.
  the feedback loop of the amplifier circuit comprises a subtractor receiving on the inputs thereof the potential of the anode and the potential reached by the body, and the feedback loop amplifier circuit comprises an operational amplifier wherein:
    the inverting input is connected to the subtractor output,
    the non-inverting input is connected to a positive direct current voltage source, and
    the output is connected to the anode.
  The system further comprises a device for determining the potential reached by the body according to the potentials of the electrodes connected with high impedance.
  The subtractor has a sufficiently high input impedance, so that the input currents in said subtractor do not disturb the measurements.
  The system comprises a first measurement resistor connected in series between the voltage source and the anode, and a second measurement resistor connected in series between the cathode and the ground, the voltage measurement at the terminals of the measurement resistors being suitable for inferring the values of the current at the anode and at the cathode respectively.

The measurement device is further suitable for simultaneously measuring the value of the current at the anode and at the cathode, and for comparing the value of the current in the anode and in the cathode to detect the existence of a leakage current or an additional current in the body.

The invention further relates to an electrophysiological analysis method intended to be implemented in a system according to the invention, the method comprising at least:

a measurement step during which the direct current voltage source delivers a series of direct current pulses to an active electrode, and during which the circuit obtains data representative of the current in the active electrodes and potentials on at least some electrodes connected with high impedance, and a step during which the conductance of the skin at the anode is determined, on the basis of the current passing through the anode and the difference in potential between the anode and the potential reached by the body, and wherein the difference in potential between the anode and the potential reached by the body is controlled by the voltage delivered by the direct current voltage source.

Advantageously, but optionally, the method according to the invention further comprises the comparison of the values of the currents passing through the anode and the cathode.

BRIEF DESCRIPTION OF THE FIGURES

Further features, aims and advantages of the present invention will emerge on reading the detailed description hereinafter, with reference to the appended figures, given by way of non-limiting examples, and wherein.

DETAILED DESCRIPTION

Figure 2:
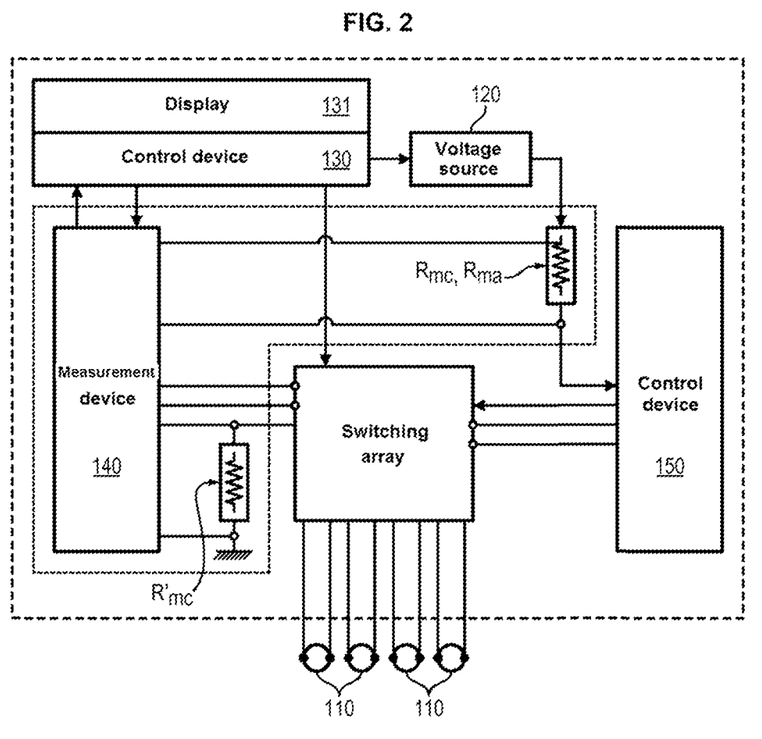
FIG. 2 schematically represents an electrophysiological analysis system.

With reference to FIG. 2, an electrophysiological analysis system 100 has been represented. This system comprises a plurality of electrodes 110, preferably four electrodes, of which two electrodes extend over a sufficiently large surface so that a subject can place his/her hands thereon, and the two other electrodes extending over a sufficiently large surface so that a subject can place his/her feet thereon. For example, these electrodes may have a surface area greater than 100 cm$^2$.

The system 100 comprises a direct current voltage source 120, suitable for generating direct current pulses. The voltage delivered by the source is preferably between 0 and 10 V, advantageously between 0 and 4 V. The pulses may have a duration greater than or equal to 0.2 seconds, and vary in voltage from one pulse to another in an increasing, decreasing or other fashion (for example increasing followed by decreasing).

The system 100 also comprises a device 130 for controlling the direct current voltage source 120 and the electrodes 110. This device is suitable for selectively connecting a pair of electrodes, forming an anode and a cathode, to the direct current voltage source so that said source can apply pulses thereto. These electrodes are referred to as "active".

The other electrodes are then connected with high impedance directly or indirectly via an operational amplifier (OA) as described hereinafter, and are suitable for measuring the potential reached by the body. They are referred to as "passive" electrodes.

FIG. 2 represents a switching array to illustrate the selective connection function of the electrodes to the direct current voltage source 120 by the control device 130. The control device 130 may implement measurement cycles by varying the pairs of active and passive electrodes. Typically, with a four-electrode system as described above, the measurements are made with the following pairs of electrodes (abbreviated description between brackets):

| Anode | Cathode |
|---|---|
| Left hand (LH) | Right hand (RH) |
| Right hand (RH) | Left hand (LH) |
| Left foot (LF) | Right foot (RF) |
| Right foot (RF) | Left foot (LF). |

The system 100 also comprises a measurement device 140 which is arranged to obtain the potentials of the passive electrodes, and to measure the current between the active electrodes. In this respect, the measurement device 140 advantageously comprises a measurement resistor $R_{mc}$ connected in series between the cathode and a reference voltage, for example the ground. The current passing through the cathode is determined by measuring the voltage at the resistor terminals, and by dividing this voltage by the resistance value.

The data measured are displayed on a display device 131. Furthermore, the system comprises a device 150 for controlling the difference in potential between the potential $V_a$ of the anode and the potential $V_x$ reached by the body, according to the voltage delivered by the direct current voltage source. This control device comprises an amplifier circuit between the direct current voltage source and one of the active electrodes, with a feedback loop involving at least one of the passive electrodes to control the amplifier gain and enable control of the difference in potential between the potential of the anode and the potential of the body Va−Vx.

The control device may be the subject of a plurality of embodiments, explained hereinafter with reference to FIGS. 3a and 3b. According to a first embodiment, with reference to FIG. 3a, the anode is connected to the ground, and the amplifier circuit comprises an operational amplifier OA, wherein the non-inverting input is connected to the negative direct current voltage source $V_g$, wherein the inverting input receives the potential Vx reached by the body, and wherein the output $V_s$ is connected to the cathode via the measurement resistor $R_{mc}$.

The control device may further comprise a device (not shown in the figure) for selecting the potential reached by the body, according to the potentials of the electrodes connected with high impedance $Vo_1$ and $Vo_2$. Preferably, the potential selected is the minimum of $Vo_1$ and $Vo_2$. Selecting the lowest potential value on the electrodes connected in high impedance makes it possible to eliminate any overvoltages of the electrodes with high impedance.

Figure 3A:
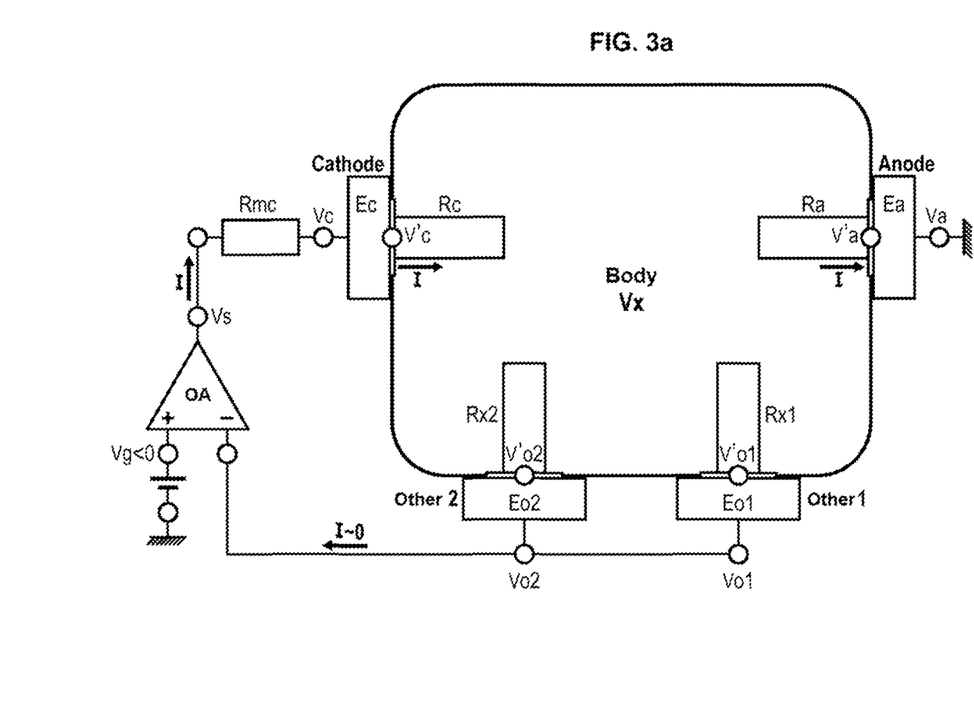
FIGS. 3a and 3b represent the minimal electrical diagram of two embodiments of an, electrophysiological analysis system according to the invention.

As seen in FIG. 3a, the measurement resistor $R_{mc}$ of the measurement device 140 is positioned between the output $V_s$ of the operational amplifier and the cathode $V_c$. By means of this arrangement, the following gain equation is obtained:

$$V_s = A(V_g - V_x),$$

where A is the gain of the operational amplifier, which is largely greater than 1 (for example in the region of several hundred thousand or one million).

The relations on the current I passing through the circuit are:

$$I = \frac{-V_s}{R_{mc} + R_c + R_a} = \frac{-V_x}{R_a}$$

where β is the feedback ratio of the feedback loop:

$$\beta = \frac{R_a}{R_a + R_c + R_{mc}}$$

where $R_a$ and $R_c$ are respectively the resistances of the sweat glands of the skin on the anode side and cathode side (to be determined), therefore this gives:

$$V_x = \beta \cdot V_s.$$

And then, by removing Vs with the gain equation, the control equation:

$$V_x = \frac{A \cdot \beta}{1 + A \cdot \beta} \cdot V_g \approx V_g \text{ as } A \gg 1.$$

In this way, the potential Vx reached by the body is set by the potential Vg delivered by the direct current voltage source. Furthermore, as the anode is connected to the ground, the potential thereof is zero, and the difference in potential $V_a - V_x$ between the anode and the potential reached by the body is equal to $-V_g$ it is thus controlled by the voltage source. It is possible in this way to study the behaviour of the sweat gland voltage-current response curve of all subjects for a constant difference in potential $V_a - V_x$.

Figure 3B:
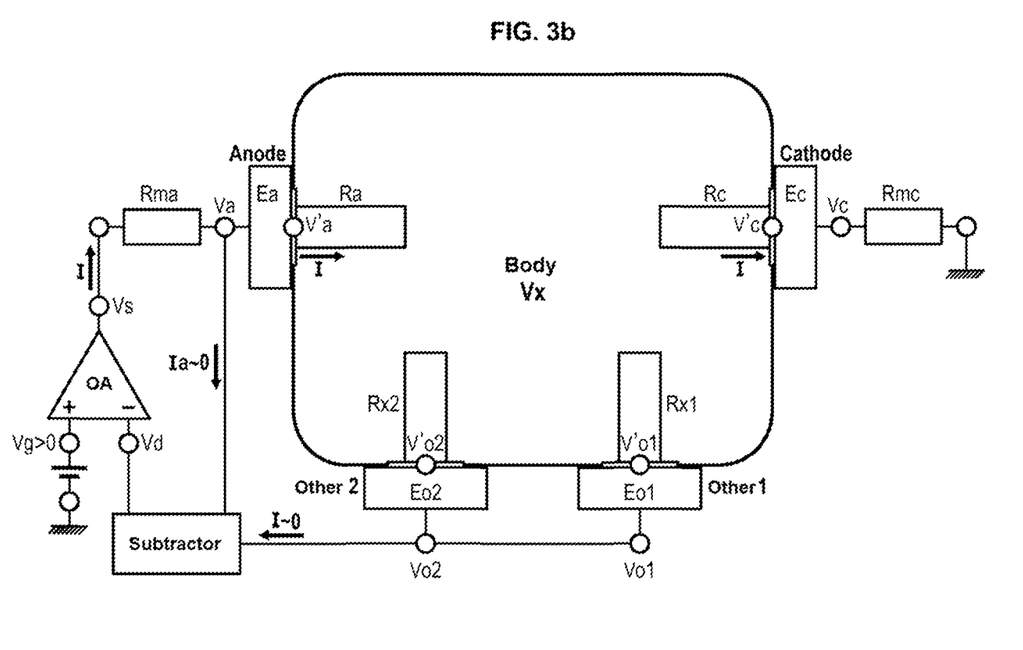

With reference to FIG. 3b, an alternative embodiment of a system equipped with a device for controlling the difference in potential $V_a - V_x$ between the anode and the potential reached by the body is represented. In this embodiment, the feedback loop of the control device comprises a subtractor receiving on the inputs thereof the potential of the anode $V_a$ and the potential reached by the body $V_x$.

The amplifier circuit of the control device comprises an operational amplifier OA, wherein the non-inverting input is connected to the direct current voltage source delivering a positive voltage, wherein the inverting input is connected to the output $V_d$ of the subtractor, and wherein the output is connected to the anode via the measurement resistor Rma. The subtractor is further suitable for having a sufficiently high input impedance, so that the input currents in said subtractor do not disturb the measurements, i.e. so that the current I between the anode and the cathode is not biased by the presence of the subtractor.

Figure 4A:
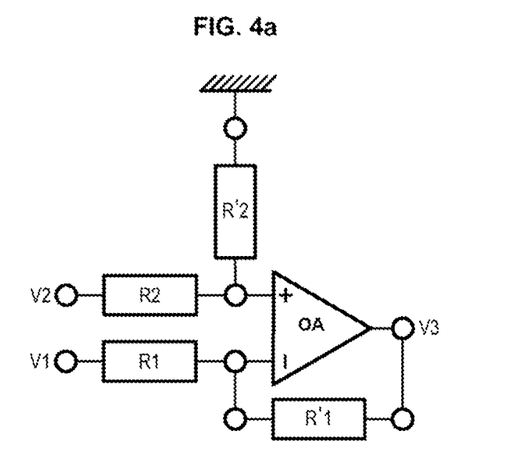
FIGS. 4a and 4b represent examples of subtractors used in the system according to the invention.
Figure 4B:
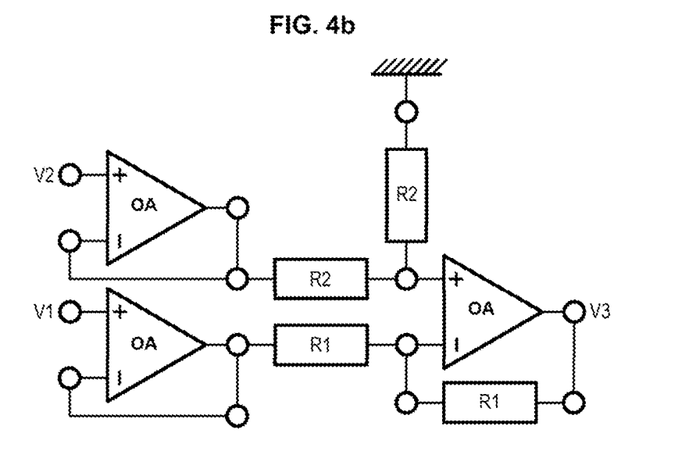

For this purpose, the subtractor may be embodied in various manners represented in FIGS. 4a and 4b. With reference to FIG. 4a, an electrical diagram of a conventional subtractor embodied by an operational amplifier is represented. In this embodiment, the output V3 of the operational amplifier is connected to the inverting input by a resistor R'1. A resistor R1 is mounted in series between the first input V1 of the subtractor and the inverting input.

Finally, a resistor R2 is mounted in series between the second input V2 of the subtractor and the non-inverting input of the operational amplifier, this input being also connected to the ground by another resistor R'2. Therefore, this gives the expression of the output V3 according to the inputs V1 and V2:

$$V3 = \frac{R1 + R'1}{R2 + R'2} \cdot \frac{R'2}{R1} \cdot V2 - \frac{R'1}{R1} \cdot V1$$

This gives, if R1=R'1 and if R2=R'2, the result V3=V2−V1.

Furthermore, if R1 and R2 are largely greater than 1, the currents extracted from the circuit $i_o$ and $i_a$ are practically zero.

A further embodiment of the subtractor is represented in FIG. 4b. It consists of the same arrangement as above, but wherein an additional operational amplifier mounted in follower mode is placed between each input V1, V2 and the corresponding resistor R1, R2.

In a follower, the output Vs of the operational amplifier is connected to the inverting terminal, and the input is connected to the non-inverting terminal. The output is connected to the input V1 by the following relations:

$$V_s = A(V1 - V_s) \text{ and}$$

$$V_s = \frac{A \cdot V1}{1 + A} \approx V1 \text{ as } A \gg 1.$$

The advantage provided by this arrangement is that it makes it possible on the control device only to extract negligible currents $i_o$ and $i_a$ of the measurement device (less than 0.1 µA), regardless of the resistance values.

With reference again to FIG. 3b, the functional equations of the arrangement are as follows:

$$V_s = A \cdot [V_g - (V_a - V_x)]$$

where A is the gain of the operational amplifier, and $$I = \frac{V_s}{R_{ma} + R_a + R_c + R_{mc}} = \frac{V_a - V_x}{R_a}.$$

In this equation, $R_{mc}$ is a first measurement resistor connected in series between the cathode and the ground, and $R_{ma}$ is a second measurement resistor connected in series between the output Vs of the operational amplifier and the anode. This second measurement resistor is optional. It is suitable for measuring the current at the anode and at the cathode to check that there has been no leakage in the system, and that the currents extracted by the subtractor are zero.

Where α is the feedback ratio of this system, this gives:

$$\alpha = \frac{R_a}{R_{ma} + R_a + R_c + R_{mc}}$$

and $$V_s = (V_a - V_x)/\alpha.$$

Hence:

$$V_a - V_x = \frac{A \cdot \alpha}{1 + A \cdot \alpha} \cdot V_g \approx V_g$$

as $A \gg 1$.

With this circuit, the voltage delivered by the direct current voltage source directly sets the difference in potential between the potential of the anode and the potential reached by the body.

Figure 5:
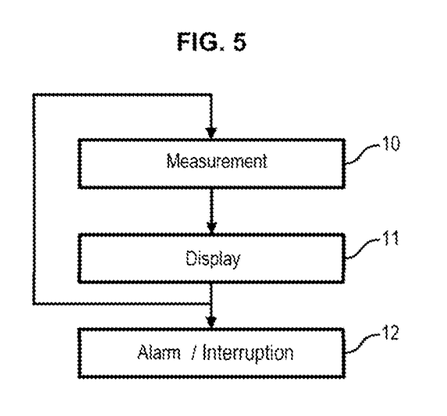
FIG. 5 represents the main steps of an analysis method implemented by a system according to the invention.

FIG. 5 shows the main steps of the method implemented with the analysis system presented above. This method comprises at least one measurement step 10, during which the direct current voltage source delivers pulses to an active electrode, two other electrodes being connected with high impedance. During this step, the control device 150 is suitable for controlling the value of the difference in potential Va–Vx between the potential of the anode and the potential reached by the body according to the voltage source.

If the circuit comprises two measurement resistors, the method may further comprise a step 11 during which the values of the current at the anode and at the cathode are compared, with a view to detecting the presence of leakage currents. The result of the comparison may be displayed on the display 131. If a leakage current is detected, measurement may be interrupted or an alert triggered during a step 12.

By means of the analysis system according to the invention, it is then possible to make use of the measurements at a constant difference in potential $V_a$–$V_x$ to conduct the analysis of the detachments in the voltage-current curves of the skin of different subjects.

The invention claimed is:

1. An electrophysiological analysis system comprising:
   (a) a series of electrodes intended to be placed in different regions of a human body;
   (b) a direct current voltage source;
   (c) a control circuit suitable for selectively applying direct current pulses, generated by the voltage source, to a pair of active electrodes, the active electrodes forming an anode and a cathode, and for connecting at least one other passive electrode with impedance, the passive electrode serving to measure potential reached by the human body, and the control circuit comprising an amplifier circuit between the direct current voltage source and one of the active electrodes, with a feedback loop controlling gain;
   (d) a measurement circuit arranged to obtain data representative of the current at the cathode and the potentials on at least some of the electrodes connected with impedance, in response to the application of the pulses, the data being suitable for use to determining a value of electrochemical conductance of skin of the human body; and
   (e) a third circuit controlling a difference between a potential of the anode and a potential reached by the body, according to the voltage delivered by the direct current voltage source.

2. The electrophysiological analysis system according to claim 1, wherein the anode is connected to ground, and the amplifier circuit comprises an operational amplifier wherein:
   (a) an inverting input receives the potential reached by the body;
   (b) a non-inverting input is connected to a negative direct current voltage source; and
   (c) an output is connected to the cathode.

3. The electrophysiological analysis system according to claim 1, wherein the feedback loop of the amplifier circuit comprises a subtractor receiving on inputs thereof the potential of the anode and the potential reached by the body, and the feedback loop amplifier circuit comprises an operational amplifier wherein:
   (a) an inverting input is connected to the subtractor output;
   (b) a non-inverting input is connected to a positive direct current voltage source; and
   (c) an output is connected to the anode.

4. The electrophysiological analysis system according to claim 1, wherein at least one of the circuits determines the potential reached by the body according to the potentials of the electrodes connected with impedance.

5. The electrophysiological analysis system according to claim 1, further comprising a subtractor having a sufficiently high input impedance, so that input currents in the subtractor do not disturb the measurements.

6. The electrophysiological analysis system according to claim 1, wherein the measurement circuit comprises a first measurement resistor connected in series between the voltage source and the anode, and a second measurement resistor connected in series between the cathode and a ground, the voltage measurement at the terminals of the measurement resistors infer the values of the current at the anode and at the cathode respectively.

7. The electrophysiological analysis system according to claim 1, wherein the measurement circuit is configured to simultaneously measure the value of the current at the anode and at the cathode, and compare the value of the current in the anode and in the cathode to detect the existence of a leakage current or an additional current in the body.

8. An electrophysiological analysis method comprising:
   (a) a measurement step during which a direct current voltage source delivers a series of direct current pulses to an anode of active electrodes, and during which the circuit obtains data representative of the current in the active electrodes and potentials on at least some electrodes connected with impedance;
   (b) a determination step during which conductance of skin at the anode is determined, on the basis of the current passing through the anode and a difference in potential between the anode and the potential reached by a body; and
   (c) controlling the difference in potential between the anode and the potential reached by the body by the voltage delivered by the direct current voltage source.

9. The method according to claim 8, further comprising comparing the values of the currents passing through the anode and a cathode of the active electrodes.

10. An electrophysiological analysis system comprising:
    (a) a series of electrodes intended to be placed in different regions of a human body;
    (b) a direct current voltage source;
    (c) at least one circuit selectively applying direct current pulses, generated by the voltage source, to a pair of active electrodes, the active electrodes forming an anode and a cathode, and for connecting at least one other passive electrode with impedance, the passive electrode serving to measure potential reached by the human body;

(d) the at least one circuit obtaining data representative of the current at the cathode and the potentials on at least some of the electrodes connected with impedance, in response to the application of the pulses, the data being suitable for use to determining a value of electrochemical conductance of skin of the human body;

(e) the at least one circuit directly setting a difference between a potential of the anode and a potential reached by the body, according to the voltage delivered by the direct current voltage source; and (f) the data assisting in evaluating sudomotor function of the human body.

11. The electrophysiological analysis system according to claim 10, further comprising:
an operational amplifier electrically connected between the voltage source and one of the active electrodes;
an inverting input receiving the potential;
a non-inverting input connected to a negative direct current voltage source; and
the electrodes include hand electrodes and feet electrodes.

12. The electrophysiological analysis system according to claim 10, wherein:
each of the electrodes has a surface area greater than 100 $cm^2$;
the direct current voltage increases and/or decreases during the measuring; and
the electrodes include hand electrodes and feet electrodes.

13. The electrophysiological analysis system according to claim 10, further comprising a controller using a detachment of a voltage-current curve of sweat glands of various human subjects for identical differences in the potential.

14. The electrophysiological analysis system according to claim 1, wherein:
each of the electrodes has a surface area greater than 100 $cm^2$;
the direct current voltage increases and/or decreases during the measuring; and
the electrodes include hand electrodes and feet electrodes.

15. The electrophysiological analysis system according to claim 1, further comprising a controller using a detachment of a voltage-current curve of sweat glands of various human subjects for identical differences in the potential.

16. The method according to claim 8, further comprising:
increasing and/or decreasing the direct current voltage during the measuring;
each of the electrodes having a surface area greater than 100 $cm^2$; and
the electrodes including hand electrodes and feet electrodes.

17. The method according to claim 8, further comprising:
the data and controlled potential difference assisting in evaluating sudomotor function of the body; and
controlling gain of an amplifier with a feedback loop including a potential input.

* * * * *